United States Patent [19]
Tashiro et al.

[11] 4,337,260
[45] Jun. 29, 1982

[54] IMIDAZOPYRIDINE-SPIRO-PIPERIDINE COMPOUNDS

[75] Inventors: Chiaki Tashiro; Ichiro Horii, both of Yoshitomi, Japan

[73] Assignee: Yoshitomi Pharmaceutical Industries, Ltd., Osaka, Japan

[21] Appl. No.: 300,824

[22] Filed: Sep. 10, 1981

[51] Int. Cl.³ .................. A61K 31/445; C07D 471/20
[52] U.S. Cl. .................................... 424/267; 546/17; 542/401
[58] Field of Search .......................... 546/17; 424/267; 542/401

[56] References Cited
U.S. PATENT DOCUMENTS 3,329,683  7/1967  Nakanishi et al. ................. 424/267
3,668,210  6/1972  Nakanishi et al. ................. 424/267
3,766,174 10/1973  Nakanishi et al. ................. 424/267
4,233,307 11/1980  Ono ..................................... 546/17

Primary Examiner—Robert T. Bond
Attorney, Agent, or Firm—Sughrue, Mion, Zinn, Macpeak & Ss

[57] ABSTRACT

An imidazopyridine-spiro-piperidine compound of the formula:

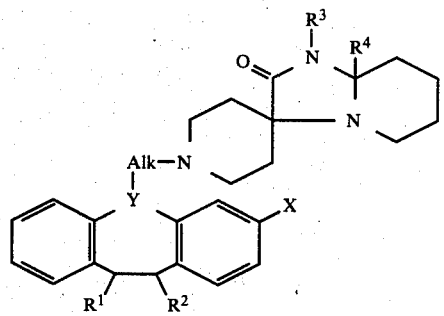

or a pharmaceutically acceptable acid addition salt thereof, wherein X represents hydrogen, halogen or lower alkoxy, Y represents >N— or >C=CH—, $R^1$ and $R^2$ both represent hydrogen or combinedly form a single bond, Alk represents lower alkylene, and $R^3$ and $R^4$ both represent hydrogen or combinedly form a single bond. Such compounds are useful as psychotropics.

10 Claims, No Drawings

IMIDAZOPYRIDINE-SPIRO-PIPERIDINE COMPOUNDS

This invention relates to novel imidazopyridine-spiro-piperidine compounds which are therapeutically useful as psychotropics.

According to the present invention, there is provided an imidazopyridine-spiro-piperidine compound of the formula:

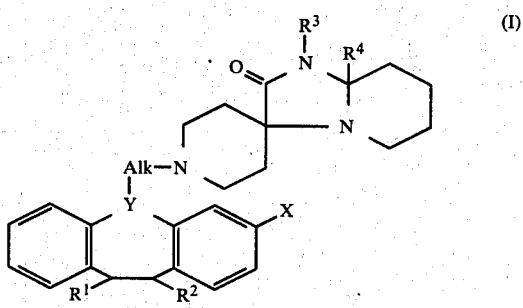

or a pharmaceutically acceptable acid addition salt thereof, wherein X represents hydrogen, halogen (e.g. F, Cl or Br) or lower alkoxy (e.g. methoxy, ethoxy, propoxy or butoxy), Y represents $>N-$ or $>C=CH-$, $R^1$ and $R^2$ both represent hydrogen or combinedly form a single bond, Alk represents lower alkylene (e.g. ethylene, propylene or trimethylene), and $R^3$ and $R^4$ both represent hydrogen or combinedly form a single bond.

The compounds of formula (I) can be produced by reacting a compound of the formula:

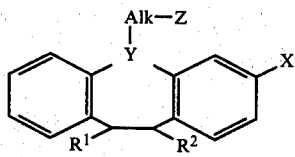

wherein X, Y, $R^1$, $R^2$ and Alk are as defined above, and Z represents a reactive atom or group (e.g. Cl, Br, methylsulfonyloxy or p-tolylsulfonyloxy), with a compound of the formula:

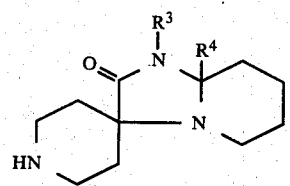

wherein $R^3$ and $R^4$ are as defined above.

The reaction is usually carried out in an inert solvent (preferably ethanol), if necessary in the presence of an acid acceptor (e.g. sodium amide, sodium hydroxide, sodium carbonate or potassium carbonate), at a temperature of from room temperature to the boiling point of the solvent employed, for a period of several hours to several tens of hours.

The novel starting compounds of formula (III) can be prepared, for example, by heating 1-benzyl-4-carbamoyl-4-piperidino-piperidine or 4-carbamoyl-4-piperidino-piperidine is an aqueous medium in the presence of a catalyst for catalytic reduction (preferably palladium-on-charcoal catalyst).

PREPARATION OF STARTING COMPOUNDS

Preparative Example A

A mixture of 10 g of 1-benzyl-4-carbamoyl-4-piperidino-piperidine, 3 g of 5% palladium-on-charcoal catalyst and 100 ml of water is boiled under reflux for 8 hours, while the toluene formed is removed. The reaction mixture is then cooled, and the catalyst is removed by filtration. The filtrate is concentrated to 10 ml under reduced pressure and is allowed to stand. The precipitated crystals are collected by filtration, dried and recrystallized from chloroform to give 2,3,5,6,7,8-hexahydro-2-oxoimidazo[1,2-a]pyridine-3-spiro-4'-piperidine as colorless crystals, m.p. 220° C., 70% yield.

Preparative Example B

A mixture of 5 g of 4-carbamoyl-4-piperidino-piperidine, 0.5 g of 5% palladium-on-charcoal catalyst and 50 ml of water is boiled under reflux for 50 hours. The reaction mixture is then cooled, and the catalyst is removed by filtration. The filtrate is concentrated and allowed to stand. The precipitated crystals are collected by filtration, dried and recrystallized from chloroform to give 1,2,3,5,6,7,8,8a-octahydro-2-oxo-imidazo[1,2-a]pyridine-3-spiro-4'-piperidine as colorless crystals, m.p. 193° C. 2,3,5,6,7,8-Hexahydro-2-oxo-imidazo[1,2-a]pyridine-3-spiro-4'-piperidine is obtained from the mother liquor. Overall yield is 65%.

The compounds of formula (I) can form pharmaceutically acceptable acid addition salts with various inorganic and organic acids such as hydrochloric, hydrobromic, sulfuric, phosphoric, maleic, fumaric, oxalic, succinic and malonic acids.

The compounds of formula (I) and pharmaceutically acceptable acid addition salts thereof show psychotropic actions.

Pharmacological Properties

1. Test Compounds

A: 1'-[3-(10,11-dihydro-5H-dibenzo[b,f]azepin-5-yl)propyl]-1,2,3,5,6,7,8,8a-octahydro-2-oxo-imidazo[1,2-a]pyridine-3-spiro-4'-piperidine dihydrochloride monohydrate.

B: 1'-[3-(3-chloro-10,11-dihydro-5H-dibenz[b,f]azepin-5yl)propyl]-1,2,3,5,6,7,8,8a-octahydro-2-oxo-imidazo[1,2-a]pyridine-3spiro-4'-piperidine dihydrochloride monohydrate C: 1'-[3-(10,11-dihydro-5H-dibenz[b,f]azepin-5-yl)propyl]-2,3,5,6,7,8-hexahydro-2-oxo-imidazo[1,2-a]pyridine-3-spiro-4'-piperidine dihydrochloride monohydrate Chlorpromazine (Comparison)

2. Methods (1) Effect on apomorphine-induced vomiting

The test was performed according to the method described by M. Nakanishi et al. in "Arzneimittel-Forschung", vol. 21, 391 ff (1971).

Groups of 5–10 beagle dogs of both sexes each were used. The test compound was administered orally 2 hours prior to the treatment with apomorphine hydrochloride (0.1 mg/kg, s.c.). The incidence of vomiting was checked for 2 hours, and the $ED_{50}$ (50% effective dose) was determined. The results are summarized in Table I.

(2) Cataleptogenic Activity

The test was performed according to the method described by W. Wirth et al. in "Archives Internationales de Pharmacodynamie et de Thérapie", vol, 115, 1 ff (1958).

Groups of 5 Wistar female rats each were used. The test compound was administered intraperitoneally, and the stages of catatonia induced with the test compound were observed in the same manner as described in the above-cited literature. The $ED_{50}$ was determined from total points of the maximum appearance of catatonia. The results are summarized in Table I.

3. Results

TABLE I

| Test Compound | Effect on Apomorphine-Induced Vomiting $ED_{50}$ (mg/kg, p.o.) | Cataleptogenic Activity $ED_{50}$ (mg/kg, i.p.) |
| --- | --- | --- |
| A | 2.5 | >50 |
| B | 0.5 | >50 |
| C | 2.0 | >50 |
| Chlorpromazine | 5.1 | 12 |

The compounds of the invention exhibit more potent than Chlorpromazine in effect on vomiting in dogs induced by apomorphine, one of desirable pharmacological properties, which permits such compounds to be employed as psychotropics. On the other hand, it is reported that the cataleptogenic activity in the animal corresponds to the side effects inducing extrapyramidal symptoms in human being. In the experiment of catalepsy inducing activity, it is revealed that the compounds of the invention are by far weaker than Chlorpromazine.

In view of various tests including those mentioned above, the compounds of the invention represented by formula (I), in base or salt form, can be safely administered as psychotropics for the treatment of schizophrenia, depression, neurosis and the like in the form of a pharmaceutical preparation with a suitable and conventional pharmaceutically acceptable carrier, without adversely affecting the patients.

The pharmaceutical preparations can take any conventional form such as tablets, capsules, granules, powders or injectable solutions.

The following is an example of formulations when a compound of the invention is administered for pharmaceutical purposes:

Tablets (25 mg) are prepared from the following compositions:

| | |
| --- | --- |
| Compound I or its salt | 25 mg |
| Lactose | 60 mg |
| Cornstarch | 23 mg |
| Microcrystalline cellulose | 10 mg |
| Methyl cellulose | 1.5 mg |
| Magnesium stearate | 0.5 mg |
| | 120 mg |

The daily dose of compound (I) or a salt thereof for human adults usually ranges from about 10 mg to about 500 mg for oral administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

A mixture of 23 g of 5-(3-chloropropyl)-10,11-dihydro-5H-dibenz[b,f]azepine, 15 g of 1,2,3,5,6,7,8,8a-octahydro-2-oxo-imidazo[1,2-a]pyridine-3-spiro-4'-piperidine and 10 g of anhydrous potassium carbonate in 100 ml of ethanol is boiled under reflux for 48 hours. The ethanol is then distilled off under reduced pressure. The residue is added to 80 ml of toluene, and the insoluble matter is filtered off. The filtrate is washed with two 50 ml portions of water, and alcoholic hydrochloric acid is added. The precipitated crystals are collected by filtration and recrystallized from methanol to give 1'-[3-(10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine dihydrochloride monohydrate as white crystals, m.p. 258° C., 70% yield.

EXAMPLE 2

A mixture of 5 g of 3-chloro-5-(3-methylsulfonyloxypropyl)-10,11-dihydro-5H-dibenz[b,f]azepine, 4 g of 1,2,3,5,6,7,8,8a-octahydro-2-oxoimidazo[1,2-a]pyridine-3-spiro-4'-piperidine, 4 g of potassium carbonate and 4 g of water in 40 ml of ethanol is stirred at 60° C. for 4 hours. The upper layer is separated and concentrated, and the residue is dissolved in 100 ml of toluene. The toluene solution is washed with water, dried, concentrated to about 15 ml and allowed to stand. The precipitated crystals are collected by filtration and recrystalized from ethanol. The crystals thus obtained are dissolved in methanol, and methanolic hydrochloric acid is added to give 1'-[3-(3-chloro-10,11-dihydro-5H-dibenz[b,f]azepin-5-yl)-propyl]-1,2,3,5,6,7,8,8a-octahydro-2-oxo-imidazo[1,2-a]pyridine-3-spiro-4'-piperidine dihydrochloride monohydrate, m.p. 261° C. This product is dried at 120° C. under reduced pressure for 4 hours to give the anhydrous product as white crystals, m.p. 271° C., 4.3 g.

EXAMPLE 3

A mixture of 3.0 g of 3-chloro-5-(3-bromopropylidene)-10,11-dihydro-5H-dibenz[a,d]cycloheptene and 3.0 g of 1,2,3,5,6,7,8,8a-octahydro-2-oxoimidazo[1,2-a]pyridine-3-spiro-4'-piperidine in 20 ml of ethanol is boiled under reflux with stirring for 5 hours. The ethanol is then distilled off under reduced pressure, and the residue is dissolved in 30 ml of toluene. The toluene solution is washed with water and extracted with 30 ml of 5% hydrochloric acid. The aqueous layer is treated with activated charcoal and made alkaline. The separated oil is allowed to stand. The crystals thus obtained is dissolved in ethanol, and ethanolic hydrochloric acid is added to give 2.8 g of 1'-[3-(3-chloro-10,11-dihydro-5H-dibenzo[a,d]cyclohepten-5-ylidene)propyl]-1,2,3,5,6,7,8,8a-octahydro-2-oxo-imidazo[1,2-a]-pyridine-3-spiro-4'-piperidine dihydrochloride as white crystals, m.p. 262° C.

Using the procedures set forth in the above examples, the following compounds are also produced:

(4) 1'-[3-(10,11-dihydro-5H-dibenz[b,f]azepin-5-yl)propyl]-2,3,5,6,7,8-hexahydro-2-oxo-imidazo[1,2-a]pyridine-3-spiro-4'-piperidine dihydrochloride monohydrate, m.p. 257° C.

(5) 1'-[3-(5H-dibenz[b,f]azepin-5-yl)propyl]-1,2,3,5,6,7,8,8a-octahydro-2-oxo-imidazo[1,2-a]pyridine-3-spiro-4'-piperidine dihydrochloride monohydrate, m.p. 233° C.

(6) 1'-[3-(5H-dibenz[b,f]azepin-5-yl)propyl]-2,3,5,6,7,8-hexahydro-2-oxoimidazo[1,2-a]pyridine-3-spiro-4'-piperidine difumarate, m.p. 192°–194° C.

(7) 1'-[3-(3-chloro-10,11-dihydro-5H-dibenz[b,f]azepin-5-yl)propyl]-2,3,5,6,7,8-hexahydro-2-oxo-imidazo[1,2-a]pyridine-3-spiro-4'-piperidine dimaleate, m.p. 135°–138° C.

(8) 1'-[3-(3-bromo-10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine dihydrochloride, m.p. 269°–270° C.

(9) 1'-[3-(3-chloro-5H-dibenz[b,f]azepin-5-yl)propyl]-1,2,3,5,6,7,8,8a-octahydro-2-oxo-imidazo[1,2-a]pyridine-3-spiro-4'-piperidine

(10) 1'-[3-(3-chloro-5H-dibenz[b,f]azepin-5-yl)propyl]-2,3,5,6,7,8,-hexahydro-2-oxo-imidazo[1,2-a]pyridine-3-spiro-4'-piperidine

(11) 1'-[3-(3-methoxy-10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine While the invention has been described in detail and with reference to specific embodiments thereof, it will be apparent to one skilled in the art that various changes and modifications can be made therein without departing from the spirit and scope thereof.

What is claimed is:

1. An imidazopyridine-spiro-piperidine compound of the formula:

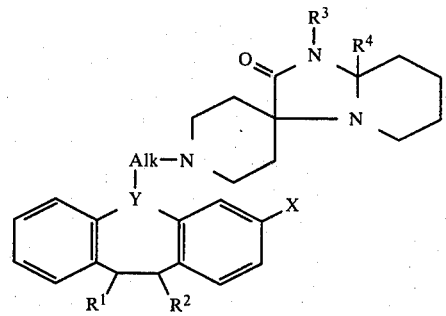

or a pharmaceutically acceptable acid addition salt thereof, wherein X represents hydrogen, halogen or lower alkoxy, Y represents >N— or >C=CH—, $R^1$ and $R^2$ both represent hydrogen or combinedly form a single bond, Alk represents lower alkylene, and $R^3$ and $R^4$ both represent hydrogen or combinedly form a single bond.

2. The compound of claim 1: 1'-[3-(10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine.

3. The compound of claim 1: 1'-[3-(3-chloro-10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine.

4. The compound of claim 1: 1'-[3-(10,11-dihydro-5H-dibenz[b,f]azepin-5-yl)propyl]-2,3,5,6,7,8-hexahydro-2-oxo-imidazo[1,2-a]pyridine-3-spiro-4'-piperidine.

5. The compound of claim 1: 1'-[3-(5H-dibenz[b,f]azepin-5-yl)propyl]-1,2,3,5,6,7,8,8a-octahydro-2-oxo-imidazo[1,2-a]pyridine-3-spiro-4'-piperidine.

6. The compound of claim 1: 1'-[3-(5H-dibenz[b,f]azepin-5-yl)propyl]-2,3,5,6,7,8-hexahydro-2-oxo-imidazo[1,2-a]pyridine-3-spiro-4'-piperidine.

7. The compound of claim 1: 1'-[3-(3-chloro-10,11-dihydro-5H-dibenz[b,f]azepin-5-yl)propyl]-2,3,5,6,7,8-hexahydro-2-oxo-imidazo[1,2-a]pyridine-3-spiro-4'-piperidine.

8. The compound of claim 1: 1'-[3-(3-bromo-10,11-dihydro-5H-dibenz[b,f]azepin-5-yl)propyl]-1,2,3,5,6,7,8,8a-octahydro-2-oxo-imidazo[1,2-a]pyridine-3-spiro-4'-piperidine.

9. The compound of claim 1: 1'-[3-(3-chloro-10,11-dihydro-5H-dibenzo[a,d]cyclohepten-5-ylidene)propyl]-1,2,3,5,6,7,8,8a-octahydro-2-oxo-imidazo[1,2-a]pyridine-3-spiro-4'-piperidine.

10. A psychotropic composition comprising the compound of claim 1 in combination with a pharmaceutically acceptable inert carrier, said compound being present in a therapeutically effective amount.

* * * * *